(12) United States Patent
Hoffman et al.

(10) Patent No.: US 8,613,767 B2
(45) Date of Patent: Dec. 24, 2013

(54) LARYNGEAL IMPLANT FOR TREATING GLOTTIC INSUFFICIENCY

(75) Inventors: Matthew Hoffman, Madison, WI (US); Jack Jiang, Wilmette, IL (US); Rachel E. Witt, Madison, WI (US); Timothy McCulloch, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 146 days.

(21) Appl. No.: 12/966,657

(22) Filed: Dec. 13, 2010

(65) Prior Publication Data

US 2012/0150293 A1 Jun. 14, 2012

(51) Int. Cl.
*A61F 2/20* (2006.01)
*A61M 16/00* (2006.01)

(52) U.S. Cl.
USPC ............... 623/9; 128/200.26; 128/207.14; 381/70

(58) Field of Classification Search
USPC ............... 623/9; 128/200.26, 207.12, 207.14; 381/70

IPC ............................................. A61F 2/20
See application file for complete search history.

(56) References Cited

U.S. PATENT DOCUMENTS

| | | | |
|---|---|---|---|
| 5,197,982 A * | 3/1993 | Goldsmith et al. | ............... 623/9 |
| 5,306,298 A | 4/1994 | Godley, III et al. | |
| 5,344,453 A | 9/1994 | Montgomery et al. | |
| 5,855,607 A | 1/1999 | Friedrich | |

\* cited by examiner

*Primary Examiner* — David Isabella
*Assistant Examiner* — Yashita Sharma
(74) *Attorney, Agent, or Firm* — Armstrong Teasdale LLP

(57) ABSTRACT

A laryngeal implant for treating glottic insufficiency includes a displacement member positionable in a larynx such that at least a portion of the displacement member is disposed between thyroid cartilage and a vocal fold of the larynx. The displacement member is at least one of selectively adjustable in volume and selectively adjustable in compressibility when the displacement member is positioned in the larynx to selectively position the vocal fold in a medial displacement position.

13 Claims, 8 Drawing Sheets

LARYNGEAL IMPLANT FOR TREATING GLOTTIC INSUFFICIENCY

STATEMENT REGARDING FEDERALLY SPONSORED RESEARCH & DEVELOPMENT

This invention was made with government support under DC005522 awarded by the National Institutes of Health. The government has certain rights in the invention.

FIELD OF THE DISCLOSURE

The field of the disclosure relates generally to laryngeal implants, and more particularly to laryngeal implants for treating glottic insufficiency.

BACKGROUND

Glottic insufficiency is a medical term used to describe insufficient closure of the glottis (i.e., the vocal folds and the space between the folds) during phonation, leading to poor voice quality and "breathiness" during phonation. Non-limiting examples of disorders that are common causes of glottic insufficiency include unilateral vocal fold paralysis, vocal fold paresis, and presbylaryngis. Typically, in each of these disorders, at least one of the vocal folds does not medialize to a normal medial position during phonation, which leads to the insufficient glottic closure.

In certain cases of glottic insufficiency, treatment is primarily surgical and aims to medialize one of the vocal folds (e.g., a paralyzed vocal fold). Current treatments include injection laryngoplasty, medialization thyroplasty with insertion of a Silastic, Gore-tex, or titanium implant, and arytenoid adduction. While injection laryngoplasty is a simple procedure which can be performed within the office, it is believed that injection laryngoplasty cannot correct severe cases of paralysis. It is also believed that injection laryngoplasty can negatively impact the mucosal wave, decreasing post-treatment voice quality. Moreover, it is believed that current implants are inhibited by several key factors: an inability to easily modify the implant according to individual patient anatomy; an inability to adjust the degree of medialization post-operatively; and potential extrusion into the airway (i.e., trachea).

SUMMARY

In one aspect, a laryngeal implant for treating glottic insufficiency generally comprises a displacement member positionable in a larynx such that at least a portion of the displacement member is disposed between thyroid cartilage and a vocal fold of the larynx. The displacement member is selectively adjustable in volume when the displacement member is positioned in the larynx to selectively position the vocal fold in a medial displacement position.

In another aspect, a method of treating glottic insufficiency generally comprises intra-operatively positioning a displacement member in a larynx such that at least a portion of the displacement member is disposed between the thyroid cartilage and a vocal fold of the larynx, and adjusting the volume of the displacement member while the displacement member is positioned in the larynx to position the vocal fold in a medial displacement position.

In yet another aspect, a laryngeal implant for treating glottic insufficiency generally comprises a displacement member positionable in a larynx such that at least a portion of the displacement member is disposed between thyroid cartilage and a vocal fold of the larynx. The displacement member is selectively adjustable in compressibility when the displacement member is positioned in the larynx to position the vocal fold in a medial displacement position.

In still another aspect, a method of treating glottic insufficiency generally comprises intra-operatively positioning a displacement member in a larynx such that at least a portion of the displacement member is disposed between the thyroid cartilage and a vocal fold of the larynx, and adjusting the compressibility of the displacement member while the displacement member is positioned in the larynx to position the vocal fold in a medial displacement position.

In another aspect, a laryngeal implant for treating glottic insufficiency generally comprises a displacement member and a mount. The displacement member is positionable in a larynx such that at least a portion of the displacement member is disposed between thyroid cartilage and a vocal fold of the larynx. The displacement member is at least one of selectively adjustable in volume and selectively adjustable in compressibility when the displacement member is positioned in the larynx to selectively position the vocal fold in a medial displacement position. The mount is for mounting the displacement member on the thyroid cartilage. The mount includes a securement base attachable to an outer surface of the thyroid cartilage, and a guide portion extending outward from the securement base and configured for insertion into an opening formed in the thyroid cartilage. The guide portion is adapted to restrict inferior and superior movement of the displacement member when the displacement member is positioned in the larynx.

DETAILED DESCRIPTION OF THE DRAWINGS

Figure 1:
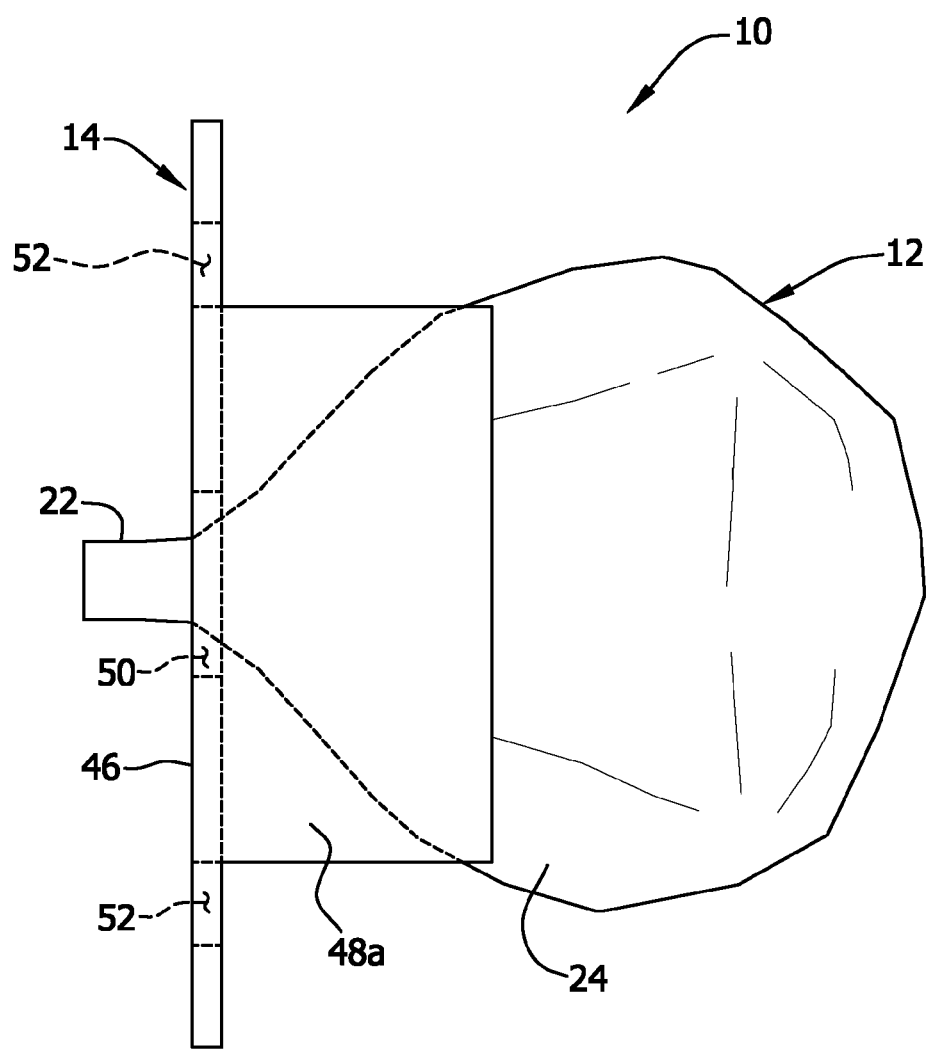
FIG. 1 is side elevation of an embodiment of a laryngeal implant for treating glottic insufficiency, including a displacement member and a mount.
Figure 7A:
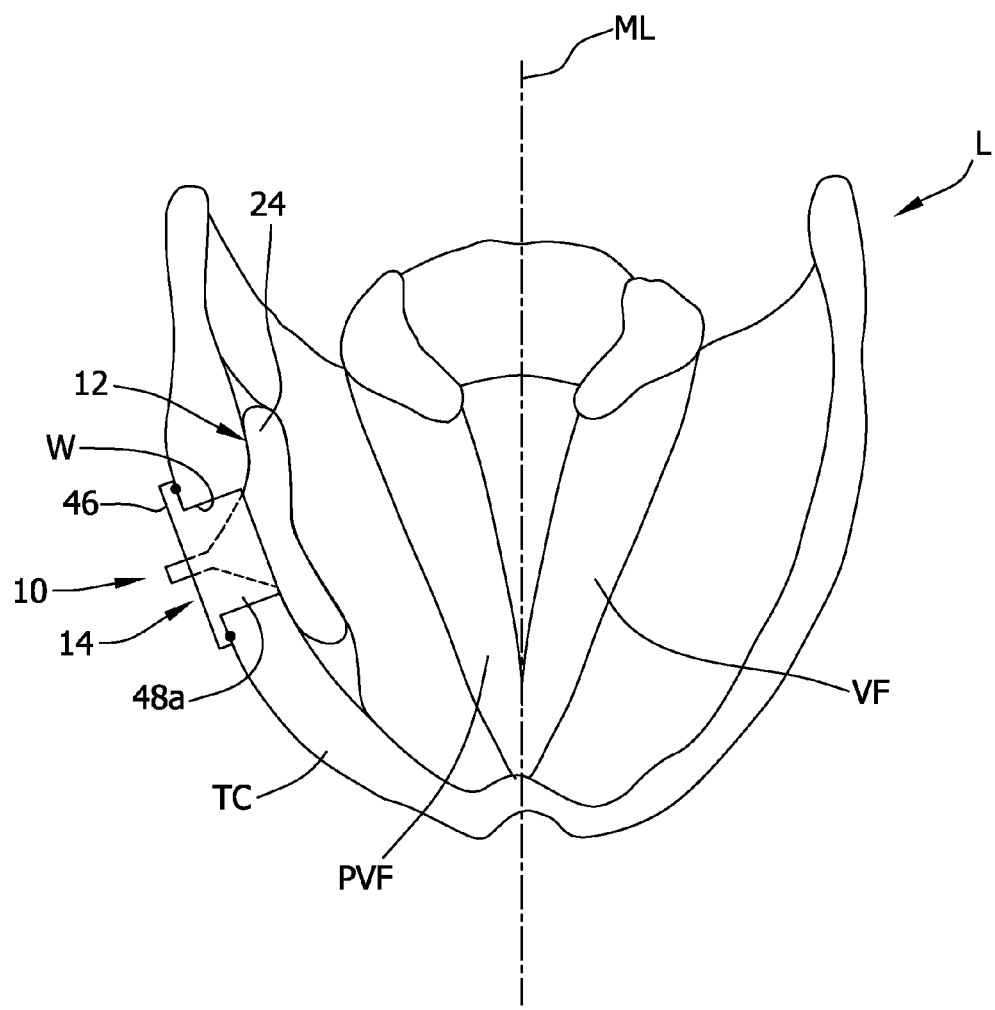
FIG. 7A is a schematic superior view of the laryngeal implant of FIG. 1 implanted in a larynx having glottic insufficiency, the laryngeal implant being in a substantially deflated configuration.
Figure 7B:
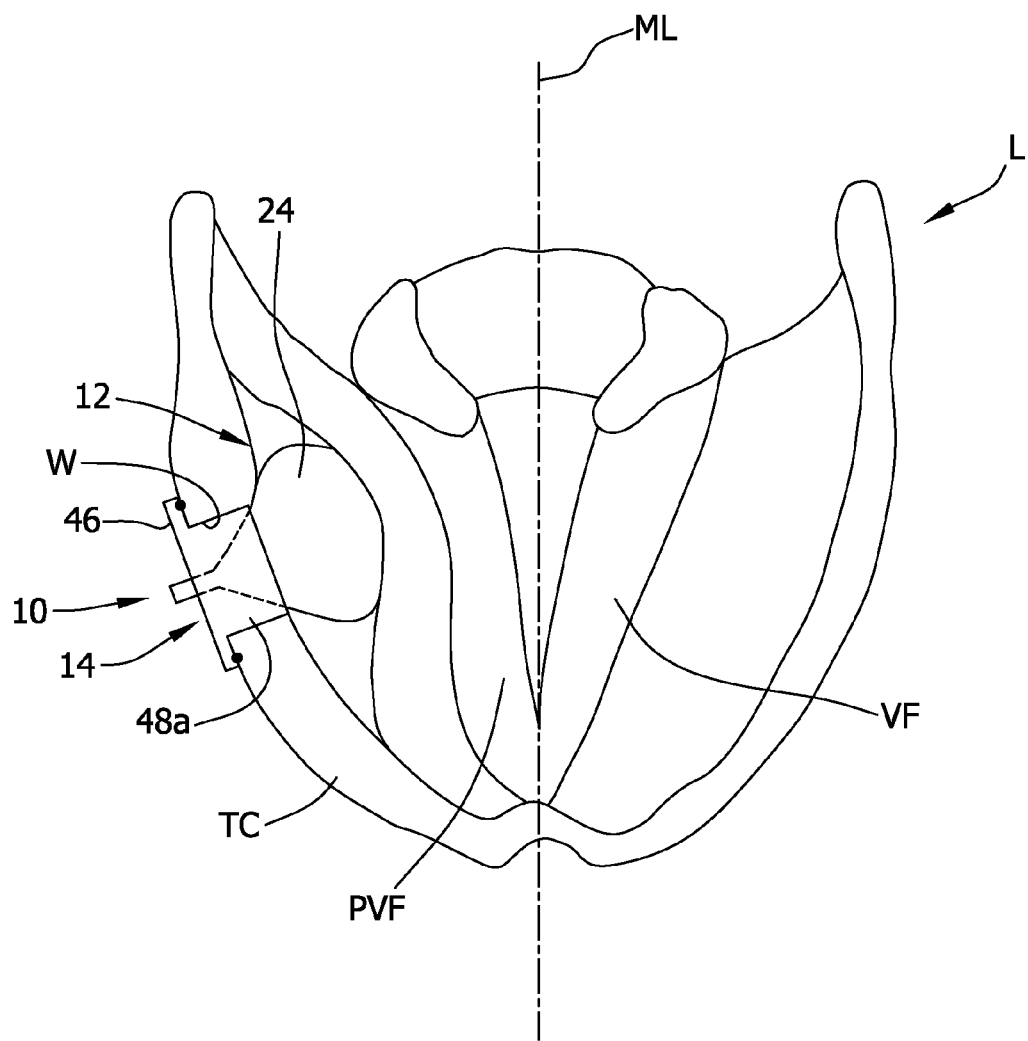
FIG. 7B is similar to FIG. 7A, except the implant is in a partially inflated configuration.
Figure 7C:
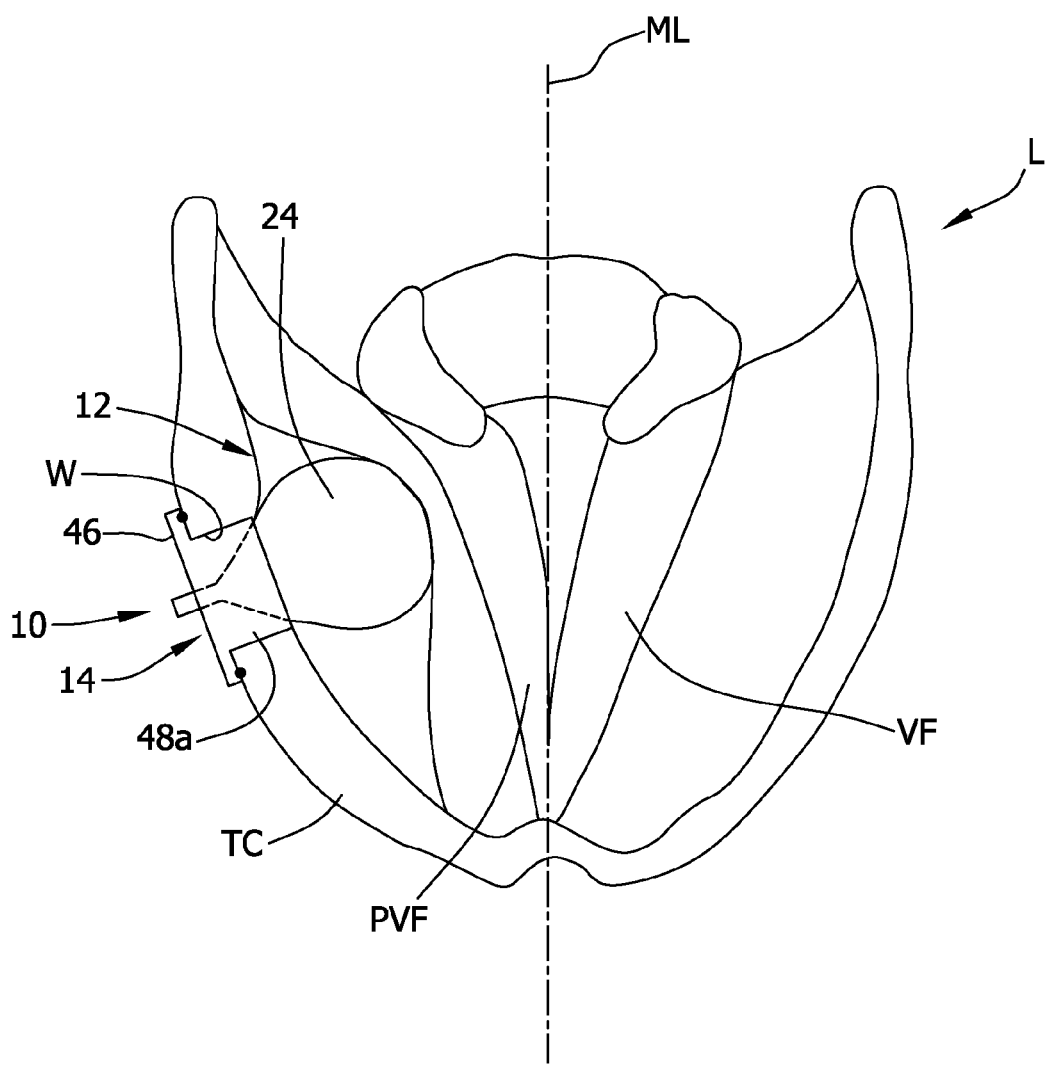
FIG. 7C is similar to FIG. 7A, except the implant is in a substantially fully inflated configuration.

Referring to FIG. 1, one embodiment of a laryngeal implant for treating glottic insufficiency is generally indicated at 10. The illustrated laryngeal implant 10 generally comprises a displacement member, generally indicated at 12, for insertion into a larynx L (FIGS. 7A-7C) of a patient, and a mount, generally indicated at 14, for mounting the displacement member on thyroid cartilage TC of the larynx L and retaining the displacement member in a desired position within the larynx. As seen in FIGS. 7A-7C, for example, the illustrated displacement member 12 is configured to selectively medially displace a paralyzed vocal fold PVF toward a midline ML (i.e., an imaginary anterior-posterior line midway between the paralyzed vocal fold PVF and a non-paralyzed vocal fold VF) and substantially retain the paralyzed vocal fold in a selected medial position. Although the illustrated laryngeal implant 10 in FIGS. 7A-7C is shown and described as treating a paralyzed vocal fold PVF, it is understood that the implant may be used in a similar manner to treat glottic insufficiency caused by other disorders, including but not limited to vocal fold paresis, and presbylaryngis. As explained in more detail below, the displacement member 12 is at least one of selectively adjustable in volume and selectively adjustable in compressibility when the displacement member is positioned in the larynx L.

Referring to FIGS. 1-4, the illustrated displacement member 12 is generally in the form of an inflatable balloon member defining an interior chamber 20. Broadly, in one embodiment the displacement member 12 is adjustable in volume when it is positioned in the larynx to position one of the vocal folds (e.g., the paralyzed vocal fold PVF in FIGS. 7A-7C) generally adjacent to the midline ML of the larynx L. As explained in more detail below, the displacement member 12 has an inlet port 22 through which fluid (e.g., gas or liquid, such as saline) is selectively introduced into the interior chamber 20 to inflate the displacement member, thereby volumetrically expanding the displacement member. The displacement member 12 is also contractible in volume, such as by removing a desired amount of fluid from the interior chamber 20. Thus, in this example the displacement member 12 may be selectively adjustable in volume to any one of a plurality of degrees of expansion by introducing and/or removing a selected volume or amount of fluid from the interior chamber 20. The amount of fluid (e.g., volume of liquid) delivered into and/or removed from the interior chamber 20 may correlate directly with the degree of expansion in volume of the displacement member 12. In this way, a degree of medialization of the paralyzed vocal fold PVF (i.e., an amount of displacement of the paralyzed vocal fold PVF), for example, can be adjusted to, and substantially retained in, a desired medial displacement position by adding and/or removing a suitable, quantitative amount of fluid from the chamber 20 to impart the desired degree of expansion of the displacement member 12.

It is understood that the displacement member 12 may be of other configurations and may be expandable in volume in other ways. For example, the displacement member 12 may include a wall or other component that is expandable upon the application of heat or electrical current, or upon the absorption of fluid, or upon a chemical reaction. It is also understood that the displacement member 12 may be only one of volumetrically expandable and volumetrically contractible, and still be considered adjustable in volume (i.e., volumetrically adjustable).

In one suitable embodiment, the displacement member 12 may be selectively adjustable in compressibility in lieu of or in addition to being selectively adjustable in volume. Broadly, in one embodiment the displacement member 12 may be adjustable in compressibility when it is positioned in the larynx to position one of the vocal folds (e.g., the paralyzed vocal fold PVF) generally adjacent to the midline ML of the larynx L. For example, in the illustrated embodiment the compressibility of the displacement member 12 may be adjusted by introducing fluid into the interior chamber 20, and/or removing fluid from the interior chamber. That is, introducing fluid into the interior chamber will decrease or reduce the compressibility of the displacement member 12, while removing fluid from the interior chamber will increase the compressibility of the displacement member. Thus, the displacement member 12 may be selectively adjustable in compressibility to any one of a plurality of degrees of compressibility by introducing and/or removing a selected volume or amount of fluid from the interior chamber 20. That is, the amount of fluid (e.g., a volume of liquid) delivered into and/or removed from the interior chamber 20 may correlate directly with the degree of compressibility of the displacement member 12. In this way, the degree of medialization of the paralyzed vocal fold PVF, for example, can be adjusted to, and substantially retained in, a desired medial displacement position by adjusting the degree of compressibility of the displacement member 12.

It is contemplated that the displacement member 12 may be configured in other ways to have a selectively adjustable compressibility. For example, the compressibility of the displacement member 12 may be adjustable by the application of heat or electrical current, or upon the absorption of fluid, or upon a chemical reaction. It is also understood that the compressibility of the displacement member 12 may be adjustable without changing the volume of the displacement member. It is further understood that the displacement member 12 may be only reducible in compressibility, or only increasable in compressibility, and would still be considered adjustable in compressibility.

The displacement member 12 may have any suitable shape and size that performs the function of positioning a vocal fold (e.g., the paralyzed vocal fold PVF) in a medial displacement position generally adjacent to the midline ML. For example, the displacement member 12 illustrated in FIGS. 1-3 has a generally spheroid shape when volumetrically expanded (see FIG. 3). The displacement member 12, however, may be of another suitable shape and size within the scope of the present invention. For example, displacement member 12 illustrated in FIG. 4 has wedge-shape. In this embodiment, the displacement member 12 may be sized and shaped such that the displacement member medially displaces the posterior third of the paralyzed vocal fold PVF more than the anterior third of the paralyzed vocal fold. Through this configuration, the displacement member 12 is less likely to cause unwanted hyperadduction of the paralyzed vocal fold PVF at the anterior third or anterior commissure. Hyperadduction of the paralyzed vocal fold PVF at the anterior third or anterior commissure may lead to unwanted pressed phonation. It is contemplated that the displacement member 12 may be configured in other ways to inhibit hyperadduction of the paralyzed vocal fold PVF at the anterior third or anterior commissure, or the displacement member may not be configured to inhibit such hyperadduction.

In the illustrated embodiment, the displacement member 12 includes at least one flexible wall 24 at least partially defining the interior chamber 20. In the illustrated embodiment, the wall 18 is a single, one-piece component that defines substantially the entire displacement member 12 and substantially the entire interior chamber 20. In this embodiment, the wall 18 may have, in one example, an outer radius of about 5 mm to about 8 mm, and more specifically, about 6 mm to about 0.28 in (7 mm), and a uniform thickness of about 0.02 in (0.5 mm) to about 0.04 in (1.0 mm). Moreover, the displacement member 12 may be configured such that the interior chamber 20 has a maximum volume of about 0.5 cc to about 2.0 cc, and more specifically, about 1.0 cc to about 1.5 cc, although the maximum volume of the interior chamber may fall outside these exemplary ranges without departing from the scope of the present invention. It is understood, however, that the displacement member may comprise more than one wall, including more than one flexible wall, and/or other components, such as one or more relatively rigid reinforcing components, without departing from the scope of the present invention. In one non-limiting example, a relatively rigid reinforcing component in combination with the flexible wall 24 may define the interior chamber. In another non-limiting example, the wall 24 may have a non-uniform thickness, such that the wall has a non-inform volumetric expansion. An anterior portion (anterior as positioned in the larynx) of the wall 18 may be thicker than a posterior portion (posterior as positioned in the larynx) so that the wall takes on a generally wedge-shaped configuration when expanded in volume to inhibit hyperadduction of the paralyzed vocal fold PVF, for example, at the anterior third or anterior commissure, as set forth above.

The wall 24 of the displacement member 12 may be resiliently stretchable in one example, and substantially non-stretchable in another example. Where the wall 24 is resiliently stretchable, the displacement member 12 may take on the preselected shape when a threshold amount of fluid is introduced into the chamber 20, and may substantially retain the shape while increasing in size (and volume) as additional fluid is introduced into the chamber. Where the wall 24 is substantially non-stretchable, the displacement member 12 may take on the preselected shape and size (and volume) when a threshold amount of fluid is introduced into the chamber 20, and may decrease in compressibility upon the introduction of additional fluid into the chamber.

As a non-limiting example, the displacement member 12 may be formed from a biocompatible material. For example, the wall 24 may be formed from silicone, or a silicone-based material, or other suitable material. Moreover, it is also contemplated that an exterior surface(s) of the displacement member may be coated with a biointegratable material, such as Gore-tex or other suitable material.

Figure 2:
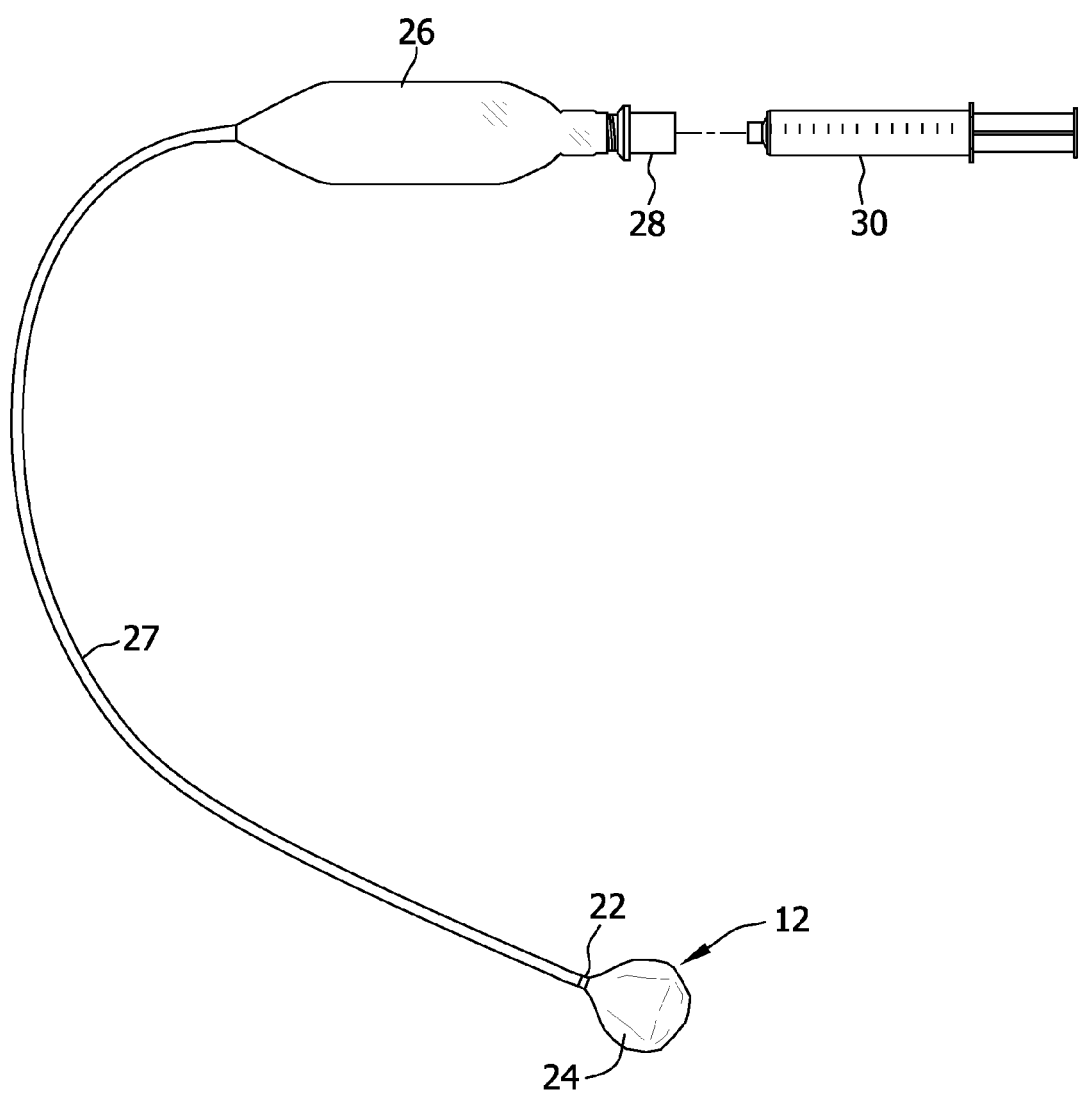
FIG. 2 is a side elevation of a second embodiment of a laryngeal implant without a mount, and a syringe for fluidly connecting to the implant.
Figure 3:
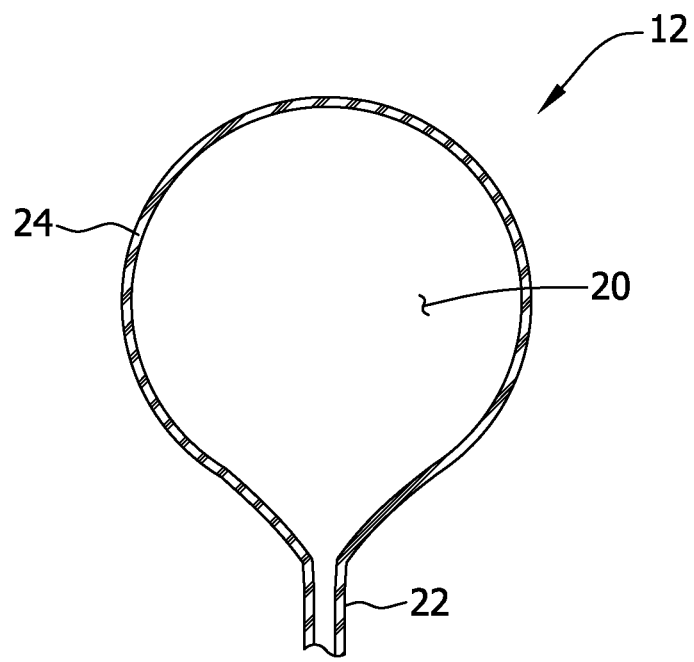
FIG. 3 is a sectional view of the displacement member of FIG. 1.

Referring to FIG. 2, in one embodiment the inlet port 22 of the displacement member 12 is fluidly connected to a fluid reservoir 26 via flexible tubing 27. The fluid reservoir 26 may be filled with a suitable amount of fluid, for example, from about 2.0 cc to about 0.5 cc of saline liquid. The reservoir 26 is resiliently compressible such that the reservoir functions as a bulb pump that delivers fluid, under pressure, into the interior chamber 20. As such, squeezing the reservoir displaces the fluid in the reservoir so that the fluid flows through the tubing 27 and into the interior chamber 20. A check valve (not shown) may be disposed between the interior chamber 20 and the reservoir 26 to inhibit unintended backflow into the reservoir, thereby substantially retaining the displacement member 12 in its expanded configuration and, in turn, retaining the paralyzed vocal fold PVF, for example, in the desired medial position. The check valve may also be selectively opened to allow removal of fluid from the interior chamber 20.

The reservoir 26 includes a fluid connector 28 that is fluidly connectable to a luer-tip syringe 30, or another source of fluid, for filling the reservoir with fluid. The fluid connector 28 includes a valve (not shown) for regulating the flow of fluid into and out of the fluid reservoir 26. The valve may be a one-way or check valve, and more specifically, a poppet valve, that is configured to open when the tip of the syringe 30 is inserted into connector 28, thereby allowing the introduction of fluid into the reservoir 26 and also allowing the removal of fluid from the reservoir. It is understood that the connector 28 may have another type of valve without departing from the scope of the present invention. Alternatively, the reservoir 26 may be pre-filled with fluid, and/or may not include the connector 28.

In another embodiment, the implant 10 may not include the fluid reservoir 26 or the tubing 27, but instead, the fluid may be delivered into the interior chamber 20 directly from a source of fluid (such as a syringe). For example, a fluid connector (not shown), which may be similar to the fluid connector 28 in FIG. 2, may be secured directly to the inlet port 22 of the displacement member 12. In another example, the tubing 27 may be connected to the inlet port 22 of the displacement member 12, and the fluid connector may be secured to the opposite end of the tubing. The implant 10 may have other configurations for use in delivering fluid into the interior chamber 20 without departing from the scope of the present invention.

Figure 5:
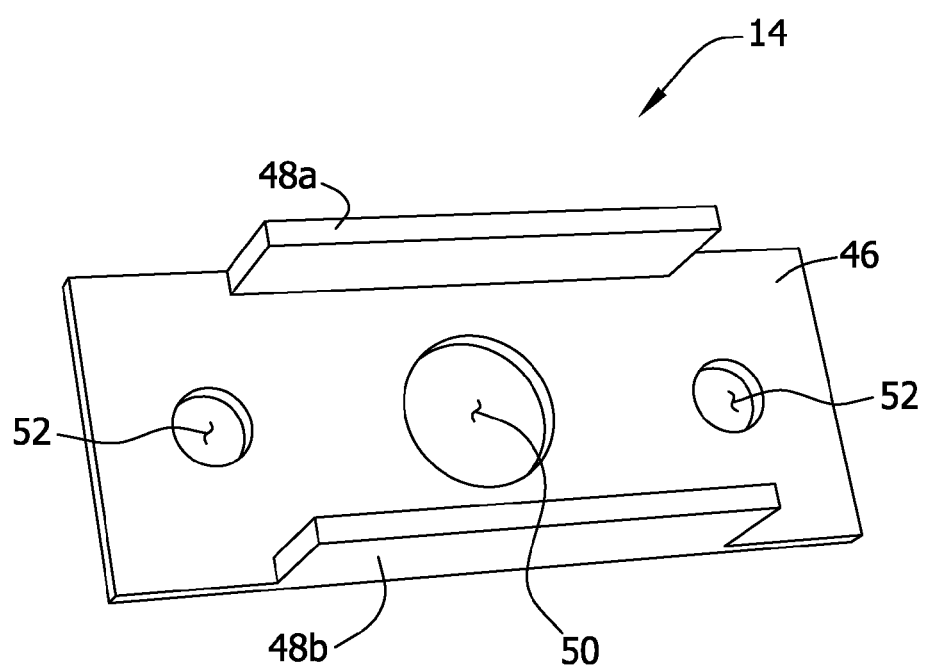
FIG. 5 is a perspective of the mount of FIG. 1.
Figure 6:
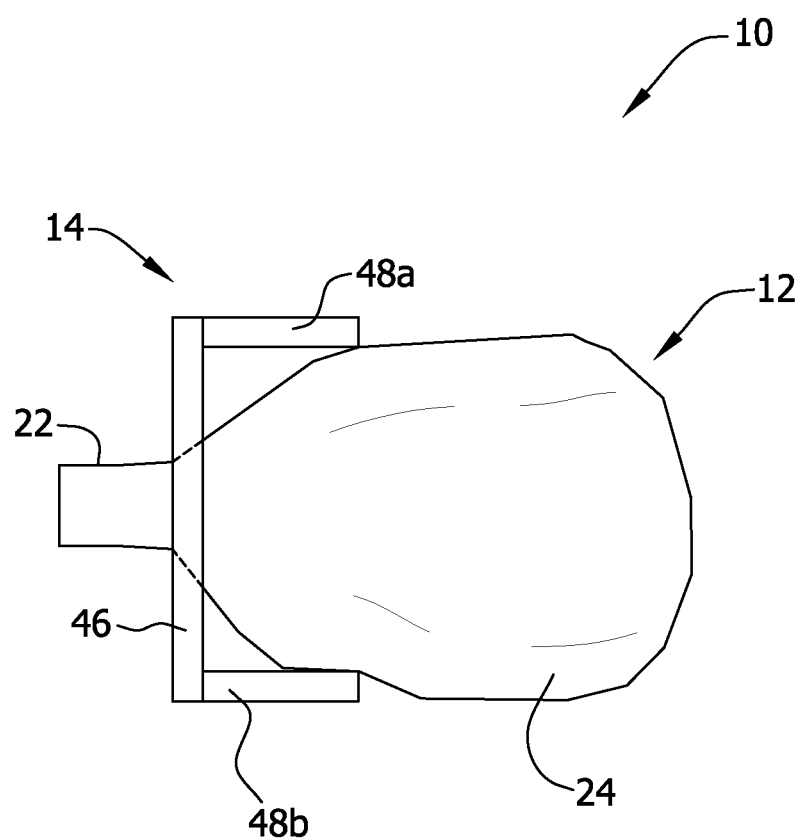
FIG. 6 is a top plan of the implant of FIG. 1.

As set forth above and seen in FIGS. 7A-7C, the mount 14 mounts the displacement member 12 on the thyroid cartilage TC and retains the displacement member in the desired position within the larynx L. Referring to FIGS. 5 and 6, the mount 14 includes a securement base 46, in the form of an elongate plate, and a pair of spaced apart, opposing guide arms 48a, 48b extending outward from a face of the base and defining a guide portion for the displacement member 12. It is understood that the guide portion may have other configurations, such as a generally rectangular periphery, without departing from the scope of the present invention. The securement base 46 has a port-receiving opening 50 for receiving the inlet port 22 of the displacement member 12, and a pair of securement openings 52 through which sutures may be inserted to secure the mount 14 to the thyroid cartilage TC. The mount 14 may be formed from a rigid material, such as metal. In one non-limiting example, the mount is formed from titanium, or another biocompatible material.

The guide arms 48a, 48b are configured for reception in a thyroplasty window W (broadly, an opening) formed in the thyroid cartilage TC during surgery. As an example, the window W may have a length of about 0.43 in (11 mm) to about 0.51 in (13 mm) extending horizontally and a width of about 0.24 in (6 mm) extending vertically. As positioned in the window W, the guide arms 48a, 48b are disposed in respective superior and inferior positions. As seen best in FIG. 6, the displacement member 12 is insertable between the guide arms 48a, 48b. During volumetric expansion of the displacement member 12, the guide arms 48a, 48b direct the displacement member 12 medially toward the paralyzed vocal fold PVF and restrict the displacement member from moving or shifting inferiorly and superiorly. Restricting superior and inferior movement of the displacement member 12 inhibits potential extrusion of the displacement member 12 into the trachea (i.e., the airway), which may lead to asphyxiation.

It is understood that the implant 10 may not include the mount 14, and may be secured to the thyroid cartilage TC in other ways, without departing from the scope of the present invention. For example, the displacement member 12 may be secured to the thyroid cartilage TC by suturing, adhesion, or in other ways. Moreover, the displacement member 12 may be retained in the desired position within the larynx L without being mounted or secured to the thyroid cartilage TC. For example, it is contemplated that the displacement member 12 may be sandwiched between the paralyzed vocal fold PVF, for example, and the thyroid cartilage TC in the larynx. In these examples, it is contemplated that an opening smaller than the thyroplasty window W may be formed in the thyroid cartilage TC, and the displacement member 12 may be inserted through this smaller opening in its deflated state or unexpanded configuration.

In an exemplary method of treating glottic insufficiency, the thyroplasty window W is formed in the thyroid cartilage TC by resecting a portion of the thyroid cartilage during surgery (i.e., intra-operatively). The displacement member 12 of the laryngeal implant 10, which has one or more features according to the teachings of the present disclosure set forth above, is inserted into the thyroplasty window W. For example, if the patient is male, a male-sized displacement member may be used, and if the patient is female, a female-sized displacement member, which is slightly smaller than the male-sized displacement member, may be used. After inserting the displacement member 12 into the thyroid cartilage window W, the guide arms 48a, 48b of the mount 14 are inserted into the window so that the arms are in superior and inferior positions, at least a portion of the displacement member 12 is located between the guide arms, and the inlet port 22 of the displacement member 12 extends through the port-receiving opening 50 of the mount 14. The mount 14 is then attached to the thyroid cartilage TC by securing sutures through the securement openings 52. Fluid (e.g., saline) is then delivered into the interior chamber 20 to expand the displacement member 12, decrease the compressibility of the displacement member, and medially displace the adjacent vocal fold (e.g., the paralyzed vocal fold PVF) toward the midline ML. Phonation of the vocal folds is tested, such as using standard testing procedures known in the art. The medial position of the paralyzed vocal fold PVF, for example, may be adjusted by adding more fluid to or removing fluid from the interior chamber 20 until the desired phonation is acquired.

After surgery (i.e., post-operatively), the inlet port 22 remains fluidly connectable to a source of fluid. For example, in the illustrated embodiment seen in FIG. 2, the inlet port 22 remains fluidly connected to the fluid reservoir 24. In another disclosed embodiment, the inlet port 22 is fluidly connected to a fluid connector, such that the source of fluid (e.g., the syringe) can selectively deliver fluid into the interior chamber 20. Thus, the volumetric expansion and/or the compressibility of the displacement member 12 can be selectively adjusted to post-operatively adjust the medial displacement position of adjacent vocal fold (e.g., the paralyzed vocal fold PVF). During surgery, swelling of tissue and other trauma experienced while inserting the displacement member may affect the phonation of the vocal folds, and after the swelling has subsided, the phonation may have changed. Thus, the implant 10 allows a practitioner to readily and relatively non-invasively correct medialization of the paralyzed vocal fold PVF, for example, post-operatively by volumetrically expanding or contracting the displacement member 12 and/or reducing compressibility or increasing compressibility of the displacement member.

After it has been determined that the adjacent vocal fold (e.g., the paralyzed vocal fold PVF) is correctly positioned, in one example the displacement member 12 may be configured to inhibit further adjustment, thereby substantially permanently retaining the paralyze vocal fold in the desired medial position. For example, the inlet port 22 may be permanently sealed, such as by using a medical adhesive or by heat welding. In the embodiment of FIG. 2, it is envisioned that the tubing 27 would be cut at a location adjacent to the inlet port 22, and then the inlet port would be permanently sealed. Other ways of inhibiting further adjustment of the displacement member 12 are within the scope of the present invention. It is understood that the displacement member 12 may remain adjustable substantially indefinitely, such as by a valve, without departing from the scope of the present invention. It is also contemplated that the displacement member 12 may also remain adjustable by sealing the tubing 27 at a location remote from the inlet port 22. In subsequent adjustments, the tubing 27 can be cut proximal to the sealed location to allow a source of fluid to be fluidly connected to the displacement member 12. After adjusting the volume of the displacement member 12, the tubing 27 can be re-sealed using the same methods described above (e.g., medical adhesive or heat welding) or in other ways.

EXPERIMENTAL RESULTS

Five larynges were excised postmortem from canines sacrificed for non-research purposes according to the protocol described by Jiang J J, Titze I R in the journal article "A Methodological Study of Hemilaryngeal Phonation", *Laryngoscope* 1993; 103:872-882. As the size and histological properties of the canine and human larynx are similar, it is an appropriate model for studying human laryngeal physiology. Both ex vivo and in vivo canine larynges have been used previously to study interventions for vocal fold paralysis. There are several anatomical differences between the human and canine larynx. The thyroid and cricoid cartilages and more angulated and not as tall in the canine larynx, and there is no well-defined vocal ligament. These differences did not negatively impact the procedure that was evaluated, as the size of the thyroid cartilage was sufficient for the creation of a thyroplasty window. Larynges were examined for evidence of trauma or disorders; any larynges exhibiting trauma or disorders were excluded. Following visual inspection, larynges were frozen in 0.9% saline solution.

Prior to the experiment, the epiglottis, corniculate and cuneiform cartilages, and ventricular folds of the larynx were removed to expose the true vocal folds. The superior cornu and posterosuperior part of the thyroid cartilage ipsilateral to the normal vocal fold were also removed to facilitate insertion of a lateral 3-pronged micrometer into the arytenoid cartilage. The larynx was mounted on the apparatus as specified by Jiang and Titze, supra. A metal hose clamp was used to stabilize the trachea to a tube connected to a pseudolung which served as a constant pressure source. Insertion of one 3-pronged micrometer in the arytenoid cartilage ipsilateral to the dissected thyroid cartilage allowed for adduction of one vocal fold, simulating UVFP in the unadducted vocal fold as taught by in Czerwonka in the journal article "A-P Positioning of Medialization Thyroplasty in an Excised Larynx Model", *Laryngoscope* 2009; 119:591-596 and Inagi et al. in the journal article "Glottal Configuration, Acoustic, and Aerodynamic Changes Induced by Variation in Suture Direction in Arytenoid Adduction Procedures", *Ann Otol Rhinol Laryngol* 2002; 111:861-870. Methodological consistency was maintained by always adducting the contralateral arytenoid (simulated normal) to the midline. Micrometer positioning remained constant across sets of trials within the same larynx. Tension on the vocal folds and control of vocal fold elongation was accomplished by connecting the thyroid cartilage, just inferior to the thyroid notch, to an anterior micrometer. Vocal fold elongation and adduction remained constant for all trials.

The pseudolung used to initiate and sustain phonation in these trials was designed to simulate the human respiratory system. Pressurized airflow was passed through two Concha Therm III humidifiers (Fisher & Paykel Healthcare Inc., Laguna Hills, Calif.) in series to humidify and warm the air. The potential for dehydration was further decreased by frequent application of 0.9% saline solution between trials. Airflow was controlled manually and measured using an Omega airflow meter (model FMA-1601A, Omega Engineering Inc., Stamford, Conn.). Pressure measurements were taken immediately before the air passed into the larynx using a Heise digital pressure meter (901 series, Ashcroft Inc., Stratford, Conn.).

Acoustic data were collected using a dbx microphone (model RTA-M, dbx Professional Products, Sandy, Utah) positioned at a 45° angle to the vocal folds. The microphone was placed approximately 10 cm from the glottis to minimize acoustic noise produced by turbulent airflow. Acoustic signals were subsequently amplified by a Symetrix preamplifier (model 302, Symetrix Inc., Mountlake Terrace, Wash.). A National Instruments data acquisition board (model AT-MIO- 16; National Instruments Corp, Austin, Tex.) and customized LabVIEW 8.5 software were used to record airflow, pressure, and acoustic signals on a personal computer. Aerodynamic data were recorded at a sampling rate of 100 Hz and acoustic data at 40,000 Hz. Experiments were conducted in a triple-walled, sound-proof room to reduce background noise and stabilize humidity levels and temperature.

The vocal fold mucosal wave was recorded for approximately 200 milliseconds per trial using a high-speed digital camera (model Fastcam-ultima APX; Photron, San Diego, Calif.). Videos were recorded with a resolution of 512×256 pixels at a rate of 4000 frames/second.

A laryngeal implant substantially similar to the implant illustrated in FIG. 2 of the present disclosure was used. The implant included a generally spheroid balloon made from silicone and having a diameter of about 0.47 in (12 mm) and wall thickness of about 0.02 in (0.5 mm). The balloon was connected via tubing to a luer slip one-way check valve. The tubing had an outside diameter of about 0.06 in (1.5 mm). Both the balloon and the tubing were made using 50 durometer medical grade silicone. The implant was placed lateral to the thyroarytenoid muscle and secured inside the larynx using an aluminum frame substantially similar to the mount illustrated in FIG. 5 of the present disclosure. Superior and inferior flanges prevented extrusion of the implant while lateral flanges with holes allowed the frame to be sutured to the thyroid lamina.

The balloon used in this experiment had a maximum volume of 1.5 cc. The amount of saline injected into the balloon depended upon the size of the larynx and width of the glottal gap. Saline was injected into the balloon via a luer slip syringe until the paralyzed fold approximated the normal fold. Fine adjustments were then made according to perceptual analysis of vocal quality and quantitative analysis of threshold aerodynamics. Care was taken to avoid overinjection and resultant balloon bulging. If bulging was observed, saline was removed until an optimal volume was reached.

Trials were conducted as a sequence of 5 second periods of phonation, followed by 5 second periods of rest. Five trials were performed for each condition. During each trial, airflow passing through the larynx was increased gradually and consistently until the onset of phonation. Larynges were thoroughly hydrated with 0.9% saline solution between trials and between sets of trials to eliminate any potentially confounding effects of dehydration.

Phonation was evaluated in three conditions: normal; simulated right vocal fold paralysis (VFP); and right VFP with the laryngeal implant. Airflow and pressure at the phonation onset were recorded as the phonation threshold flow (PTF) and phonation threshold pressure (PTP), respectively. Phonation threshold power (PTW) was calculated as the product of these values. PTF, PTP, and PTW were determined manually using customized LabVIEW 8.5 software, available from National Instruments Corporation of Austin, Tex., USA.

Measured acoustic parameters included fundamental frequency (F0), signal-to-noise ratio (SNR), percent jitter, and percent shimmer. Acoustic signals were trimmed to produce three 1-second segments per trial using GoldWave 5.1.2600.0 software (GoldWave Inc., St. John's, Canada) and these segments were analyzed using TF32 software (Madison, Wis.).

High speed video recordings of the mucosal wave were analyzed using a customized MATLAB program (The MathWorks, Natick, Mass.). Vibratory properties of each of the four vocal fold lips (right-upper, right-lower, left-upper, left-lower) were quantified via digital videokymography (VKG). Threshold-based edge detection, manual wave segment extraction, and non-linear least squares curve fitting using the Fourier Series equation were applied to determine the most closely fitting sinusoidal curve. This curve was used to derive the amplitude and phase difference of the mucosal wave of each vocal fold lip, both before and after treatment. Mucosal wave amplitude was calculated as the average of the amplitudes of the upper and lower paralyzed vocal fold lips. While only relative rather than absolute values could be obtained due to current technological limitations, this was sufficient for pre-/post-treatment comparisons.

One-way repeated measures analysis of variance (ANOVA) was performed to determine if there were differences in the parameters of interest across the three conditions. Paired t-tests were performed to determine if significant differences occurred between paired conditions (normal vocal fold and VFP, VFP and laryngeal implant, normal and laryngeal implant). If data were not normal according to a Shapiro-Wilk test or did not display equal variance according to a Levene's test, an ANOVA on ranks or Wilcoxon-Mann-Whitney paired rank sum test was performed. Tests were two-tailed and a significance level of $\alpha = 0.05$ was used.

Figure 4:
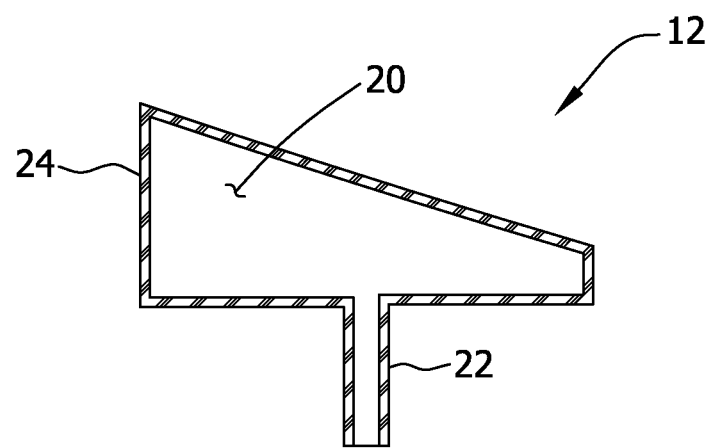
FIG. 4 is a sectional view of another embodiment of a displacement member.

Summary data relating to aerodynamics are presented in Table 1, below. The laryngeal implant significantly decreased PTP ($p=0.038$), PTF ($p<0.001$), and PTW ($p=0.016$) relative to the VFP condition (table 2; FIG. 4). PTF ($p=0.039$) and PTW ($p=0.038$) remained significantly higher relative to normal (Table 2).

Summary data relating to acoustics are also presented in Table 1, below. The laryngeal implant had significant effects on SNR ($p=0.005$), percent jitter ($p=0.034$), and percent shimmer ($p=0.037$) (table 2; FIGS. 5, 6). These values were restored to the levels observed for the normal condition (Tables 1 and 2). Fundamental frequency decreased discernibly.

Summary data relating to mucosal wave are presented in Table 1, below. Mucosal wave amplitude of the normal fold discernibly increased from the normal to paralyzed condition ($p=0.055$). Amplitude of this fold remained elevated after insertion of the laryngeal implant (Table 1). Amplitude of the right vocal fold (simulated paralysis) was the same in the normal and ASI conditions ($p=0.966$).

TABLE 1

Summary aerodynamic, acoustic, and mucosal wave data including p-values obtained from one-way repeated measures analysis of variance (ANOVA) statistical tests.

| Parameter | Normal | VFP | ASI | p-value |
|---|---|---|---|---|
| PTF (ml/s) | 17.12 ± 6.86 | 99.12 ± 57.51 | 25.08 ± 4.14 | <0.001* |
| PTP (cmH$_2$0) | 7.976 ± 3.38 | 20.72 ± 11.88 | 10.71 ± 5.09 | 0.002* |
| PTW (cmH$_2$O * ml/s) | 142.8 ± 88.9 | 2298 ± 2355 | 281.9 ± 167.7 | 0.002* |
| F$_0$ (Hz) | 306 ± 96 | 177 ± 26 | 246 ± 45 | 0.024* |
| SNR | 13.71 ± 4.94 | 3.945 ± 1.94 | 13.43 ± 4.06 | 0.003* |
| Percent jitter | 1.089 ± 0.98 | 3.156 ± 1.38 | 0.968 ± 0.480 | 0.024* |
| Percent shimmer | 19.26 ± 4.99 | 49.41 ± 19.1 | 21.47 ± 4.91 | 0.007* |
| Amplitude (R) | 3.794 ± 1.93 | 4.511 ± 1.62 | 3.878 ± 3.92 | 0.367 |
| Amplitude (L) | 3.509 ± 1.22 | 6.812 ± 2.17 | 6.176 ± 5.65 | 0.275 |

VFP = vocal fold paralysis;
ASI = adjustable saline implant;
PTF = phonation threshold flow;
PTP = phonation threshold pressure;
F0 = fundamental frequency;
SNR = signal-to-noise ratio;
R = right vocal fold (simulated paralysis in VFP and laryngeal implant conditions);
L = left vocal fold.
Asterisks indicate significant p-values.

TABLE 2

P-values obtained from paired t-tests between treatments.

| Parameter | Normal, VFP | VFP, ASI | Normal, ASI |
|---|---|---|---|
| PTP (cmH$_2$0) | 0.007* | 0.038* | 0.103 |
| PTF (ml/s) | <0.001* | <0.001* | 0.039* |
| PTW (cmH$_2$O * ml/s) | 0.016* | 0.016* | 0.038* |
| F$_0$ (Hz) | 0.044* | 0.069 | 0.169 |
| SNR | 0.018* | 0.005* | 0.901 |
| Percent jitter | 0.092 | 0.034* | 0.733 |
| Percent shimmer | 0.031* | 0.037* | 0.349 |
| Amplitude (R) | 0.597 | 0.735 | 0.966 |
| Amplitude (L) | 0.055 | 0.777 | 0.813 |

VFP = vocal fold paralysis;
ASI = adjustable saline implant;
PTF = phonation threshold flow;
PTP = phonation threshold pressure;
F0 = fundamental frequency;
SNR = signal-to-noise ratio;
R = right vocal fold (simulated paralysis in VFP and laryngeal implant conditions);
L = left vocal fold.
Asterisks indicate significant p-values.

Based on experimental observations, glottal gap was decreased upon insertion of the laryngeal implant, placing the paralyzed vocal fold in a position more conducive for voicing and increasing phonatory efficiency. PTP, PTF, and PTW were all significantly decreased. According to the recorded data, the implant not only improved the acoustic parameters of interest, but also restored SNR, percent jitter, and percent shimmer to normal or near normal levels. While it did increase F$_0$, the resultant frequency was discernibly, though not significantly, less than normal. Improvement of perturbation parameters to approximately normal levels can be attributed to restoration of vocal fold contact and vibrational periodicity. Increased SNR occurred due to decreased airflow required for phonation as well as increased acoustic output.

Insignificant increases in the mucosal wave amplitude of the right and left vocal folds were observed from the normal to paralyzed condition. Based on experimental observations, this appeared to be due to the high airflow through the glottis required for phonation. However, without vocal fold contact, vocal quality was poor despite the large amplitude. Insertion of the implant closed the glottal gap and preserved mucosal wave amplitude, resulting in improved vocal quality. Following insertion of the laryngeal implant, the mucosal wave was preserved.

This written description uses examples to disclose the invention, including the best mode, and also to enable any person skilled in the art to use the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A laryngeal implant for treating glottic insufficiency, the implant comprising:
a displacement member positionable in a larynx such that at least a portion of the displacement member is disposed between thyroid cartilage and a vocal fold of the larynx, the displacement member being selectively adjustable in volume when the displacement member is positioned in the larynx to selectively position the vocal fold in a medial displacement position; and
a mount for mounting the displacement member on the thyroid cartilage, the mount comprising:
a securement base attachable to an outer surface of the thyroid cartilage, the securement base having an opening defined therethrough; and
a pair of substantially parallel spaced apart opposing guide arms extending substantially perpendicularly outward from a face of the securement base,
wherein a portion of the displacement member is configured to extend through the opening defined in the securement base.

2. The laryngeal implant set forth in claim 1 wherein the displacement member is selectively expandable in volume to any one of a plurality of degrees of volumetric expansion when the displacement member is positioned in the larynx.

3. The laryngeal implant set forth in claim 2 wherein the displacement member is selectively contractible in volume from one of the plurality of degrees of volumetric expansion to a lesser one of the plurality of degrees of volumetric expansion when the displacement member is positioned in the larynx.

4. The laryngeal implant set forth in claim 2 wherein the displacement member is substantially retainable in a selected one of the plurality of degrees of volumetric expansion to substantially retain the vocal fold in a desired medial displacement position.

5. The laryngeal implant set forth in claim 1 wherein the displacement member defines an interior chamber, the displacement member being configured for receiving of fluid into the interior chamber when the displacement member is positioned in the larynx to volumetrically expand the displacement member.

6. The laryngeal implant set forth in claim 5 wherein the displacement member includes at least one flexible wall at least partially defining the interior chamber.

7. The laryngeal implant set forth in claim 6 further comprising a fluid port in fluid communication with the interior chamber, the port being configured for fluid communication with a source of fluid to facilitate flow of fluid into the interior chamber.

8. The laryngeal implant set forth in claim 7 further comprising a valve in fluid communication with the port and the interior chamber, the valve being adapted to regulate the flow of fluid at least one of into the interior chamber and out of the interior chamber.

9. The laryngeal implant set forth in claim 1 wherein the guide arms are configured for insertion into an opening formed in the thyroid cartilage, the guide arms being adapted to restrict inferior and superior movement of the displacement member when the displacement member is positioned in the larynx.

10. The laryngeal implant set forth in claim 9 wherein at least a portion of the displacement member is retained between the opposing guide arms.

11. The laryngeal implant set forth in claim 7 wherein the fluid port of the displacement member is configured to extend through the opening defined in the securement base.

12. The laryngeal implant set forth in claim 1 wherein the displacement member is selectively adjustable in compressibility when the displacement member is positioned in the larynx.

13. A laryngeal implant for treating glottic insufficiency, the implant comprising:
a displacement member positionable in a larynx such that at least a portion of the displacement member is disposed between thyroid cartilage and a vocal fold of the larynx, the displacement member being selectively adjustable in volume when the displacement member is positioned in the larynx to selectively position the vocal fold in a medial displacement position; and a mount for mounting the displacement member on the thyroid cartilage, the mount comprising:
  a securement base attachable to an outer surface of the thyroid cartilage; and
  a pair of substantially parallel spaced apart opposing guide arms extending substantially perpendicularly outward from a face of the securement base, wherein the opposing guide arms are configured for insertion into an opening formed in the thyroid cartilage, and wherein at least a portion of the displacement member is retained between the opposing guide arms.

* * * * *